United States Patent
Selstam et al.

(10) Patent No.: US 9,199,888 B2
(45) Date of Patent: Dec. 1, 2015

(54) COMBINED PROCESSES FOR UTILIZING SYNTHESIS GAS WITH LOW CO₂ EMISSION AND HIGH ENERGY OUTPUT

(71) Applicant: SGE ScandGreen Energy AB, Mölnlycke (SE)

(72) Inventors: Henrik Selstam, Mölnlycke (SE); Erik Fareid, Langesund (NO)

(73) Assignee: SGE ScandGreen Energy AB, Molnlycke (SE)

( * ) Notice: Subject to any disclaimer, the term of this patent is extended or adjusted under 35 U.S.C. 154(b) by 0 days.

(21) Appl. No.: 14/373,926

(22) PCT Filed: Jan. 24, 2013

(86) PCT No.: PCT/EP2013/051360
§ 371 (c)(1),
(2) Date: Jul. 23, 2014

(87) PCT Pub. No.: WO2013/110716
PCT Pub. Date: Aug. 1, 2013

(65) Prior Publication Data
US 2014/0364517 A1    Dec. 11, 2014

Related U.S. Application Data

(60) Provisional application No. 61/590,349, filed on Jan. 25, 2012.

(30) Foreign Application Priority Data

Jan. 24, 2012  (SE) ...................................... 1250049

(51) Int. Cl.
| | | |
|---|---|---|
| *C07C 1/04* | (2006.01) | |
| *C10J 3/18* | (2006.01) | |
| *C10K 3/04* | (2006.01) | |
| *C10K 1/00* | (2006.01) | |
| *C10G 2/00* | (2006.01) | |
| *C01B 3/02* | (2006.01) | |

(52) U.S. Cl.
CPC .................. *C07C 1/0485* (2013.01); *C01B 3/02* (2013.01); *C07C 1/041* (2013.01); *C10G 2/30* (2013.01); *C10J 3/18* (2013.01); *C10K 1/004* (2013.01); *C10K 3/04* (2013.01); *C01B 2203/0255* (2013.01); *C01B 2203/0283* (2013.01); *C01B 2203/061* (2013.01); *C01B 2203/062* (2013.01); *C01B 2203/1052* (2013.01); *C01B 2203/1064* (2013.01); *C01B 2203/1094* (2013.01); *C10J 2300/0916* (2013.01); *C10J 2300/0946* (2013.01); *C10J 2300/0969* (2013.01); *C10J 2300/1238* (2013.01); *C10J 2300/1618* (2013.01); *C10J 2300/1659* (2013.01); *C10J 2300/1662* (2013.01); *C10J 2300/1665* (2013.01); *Y02E 50/18* (2013.01); *Y02E 50/32* (2013.01)

(58) Field of Classification Search
CPC .............. C07C 1/04; C10G 2/00; C10G 2/32; C10G 2/33
See application file for complete search history.

(56) References Cited

U.S. PATENT DOCUMENTS

| | | |
|---|---|---|
| 4,532,229 A | 7/1985 | Fiato et al. |
| 6,958,136 B2 | 10/2005 | Chandran et al. |
| 7,872,054 B2 | 1/2011 | Cortright et al. |
| 8,084,508 B2 | 12/2011 | Yakobson et al. |
| 2007/0129449 A1 | 6/2007 | Topf et al. |
| 2007/0186472 A1 | 8/2007 | Rabovitser et al. |
| 2009/0100752 A1 | 4/2009 | Sessa et al. |
| 2010/0313840 A1 | 12/2010 | Day et al. |
| 2011/0067376 A1 * | 3/2011 | Tompkins et al. ........... 60/39.12 |

FOREIGN PATENT DOCUMENTS

| | | |
|---|---|---|
| EP | 0221679 A2 | 5/1987 |
| WO | 2008087147 A1 | 7/2008 |
| WO | 2008130260 A1 | 10/2008 |
| WO | 2009102383 A1 | 8/2009 |
| WO | 2010059224 A1 | 5/2010 |
| WO | WO 2010059224 A1 * | 5/2010 |
| WO | 2010107777 A1 | 9/2010 |
| WO | 2011002527 A1 | 1/2011 |
| WO | 2011008263 A2 | 1/2011 |
| WO | 2011016759 A1 | 2/2011 |

OTHER PUBLICATIONS

Schubert, Paul F., et al. "Fischer-Tropsch Diesel Fuel Preparation and Testing." Abstracts of Papers of the American Chemical Society. vol. 220. 1155 16th St, NW, Washington, DC 20036 USA: Amer Chemical Soc, 2000.

\* cited by examiner

*Primary Examiner* — Sudhakar Katakam
(74) *Attorney, Agent, or Firm* — Kagan Binder, PLLC

(57) ABSTRACT

A process and system for producing liquid and gas fuels and other useful chemicals from carbon containing source materials comprises cool plasma gasification and/or pyrolysis of a source material to produce synthesis gas using the produced synthesis gas for the production of a hydrocarbon, methanol, ammonia, urea, and other products. The process and system are capable of sequestering carbon dioxide and reducing NOx and SOx.

13 Claims, 1 Drawing Sheet

COMBINED PROCESSES FOR UTILIZING SYNTHESIS GAS WITH LOW $CO_2$ EMISSION AND HIGH ENERGY OUTPUT

FIELD OF THE INVENTION

The present invention relates generally to the conversion of carbon containing waste materials into useful fuels. More specifically, the invention provides for methods, systems, and apparatus for the conversion of materials containing carbon to diesel and other useful fuels using synthesis gas as an intermediate.

BACKGROUND OF THE INVENTION

The reality of global climate change is motivating efforts to reduce the emission of human-produced $CO_2$ and other greenhouse gases into the atmosphere. The combustion of fossil fuels such as coal, gasoline, and diesel is a major source of $CO_2$ emissions and contributes to increasing levels of $CO_2$ in the atmosphere. Carbon neutral alternatives to fossil fuels, including biodiesel and ethanol are limited by their limited supply, costs of production, and their requirement for farmland that may be needed for food production. There remains a need for carbon neutral alternatives to diesel, gasoline, and other fuels produced from oil.

Processes for the production of synthesis gas (syngas) are known in the art. For example, WO 2011/008263 A2 discloses the use of plasma gasification or pyrolysis for production of synthesis gas followed by the production of hydrogen from the synthesis gas in a water gas shift reaction and the production of products in various types of reactors.

WO 2011/002527 A1 discloses a method in which syngas is generated from a waste and water using a plasma melter, hydrogen is extracted from the syngas using a water gas shift reaction, and a C9 fuel is synthesized from the extracted hydrogen and syngas in a Fischer-Tropsch type reactor. The carbon for fuel synthesis is provided by the exhaust from a plant exhaust (e.g. a power plant exhaust), which is passed through a plasma chamber and then to a Fischer Tropsch reactor.

WO 2009/091325 A1 discloses a biomass gasification method and apparatus for production of syngas with a rich hydrogen content; and U.S. Pat. No. 5,584,255 discloses a method and apparatus for gasifying organic materials. U.S. Pat. No. 6,958,136 discloses a process for the treatment of nitrogen-containing waste streams that can generate syngas from carbon sources using alkalai metals and carbon radical formation.

Processes for synthesizing methane from syngas are known. For example, the methanation reaction converts syngas into methane and water in the presence of a catalyst (e.g. Ni/NiO, Ru, Cu, Pt, Rh) at temperatures between 150° C. and 600° C. PCT/NO2007/000387 discloses a process for making methane from CO, $CO_2$ and $H_2$ involving the production of $H_2$ and $O_2$ by splitting water. Jianjun Guo et al. (2004) Applied Catalysis A: General 273(1-2): 75-82 discloses the production of methane over nickel catalyst on magnesium aluminate spines. M. Wisniewski et al. (2005) Catalysis Communications 6(9): 596-600 discloses Catalytic $CO_2$ reformation of methane over $Ir/Ce_{0.9}Gd_{0.1}O_{2-x}$. U.S. Pat. No. 7,087,651 discloses a process and apparatus for steam-methane reforming.

Syngas may also be converted into a wide range of useful liquid hydrocarbons fuels and/or alcohols using the Fisher-Tropsch (F-T) process. US 2007/0129449 discloses a method and installation for producing liquid energy carriers such as methanol from a solid carbon carrier. The method involves the production of $O_2$ and $H_2$ by water electrolysis and gasifying a carbon carrier such as biomass or brown coal in a fluidized-bed gasifier in the presence of the produced $O_2$. The raw synthesis gas is transferred to a heat exchanger where the temperature is reduced and the cooled syngas is mixed with the produced $H_2$ to form methanol. The production of hydrocarbon fuels such as diesel and gasoline are not described, however, and the installation as described is not suitable for F-T reactions forming diesel or gasoline. The process is dependent on the production of $O_2$ and $H_2$ by electrolysis, which requires significant amounts of electrical power. The use of a fluidized thermal catalytic gasifier for the production of synthesis gas involves thermal catalytic methods such as counter-current fixed bed ("up draft") gasification, co-current fixed bed ("down draft") gasification, and entrained flow gasification, which produce significant amounts of tar that must be disposed of or used.

WO 2008130260 A1 discloses a waste to liquid hydrocarbon refinery system designed to convert municipal and industrial wastes, biomass, and other carbon-containing feedstocks into diesel, gasoline, and other products. The system involves a high temperature liquid iron bed that generates raw syngas from solid and liquid feedstocks and a very high temperature plasmatron to convert contaminants in the raw syngas into ions. A hydrocarbon synthesis subsystem converts the purified syngas into desired products. The system is designed to minimize the release of toxic waste into the environment but is relatively complex and expensive, requires relatively large amount of energy, and releases considerable amounts of carbon into the atmosphere.

EP 0221679 A2 discloses a process for producing liquid hydrocarbons from biomass involving the production of synthesis gas from biomass and synthesizing liquid fuels from the produced synthesis gas. Syngas is produced using a fluidized bed gasification system containing olefins. Liquid fuel containing C7 to C17 paraffinic hydrocarbons is produced from the synthesis gas, along with propanol and water, using a catalytic liquefaction. The process is designed to be economically viable but does not deal with pollutants such as NOx and SOx produced from biomass or the production of fuels from carbon-containing sources comprising municipal or industrial wastes. The process is not designed to be carbon neutral.

There remains, therefore, a need for carbon-neutral processes, apparatus, and systems for producing liquid hydrocarbon fuels from carbon-containing materials including biomass, wastes from municipal, medical and industrial sources, and coal. Additionally, there remains a need for processes, apparatus, and systems that remove NOx and/or SOx produced by the combustion of renewable and fossil fuels containing nitrogen and/or sulfur. The present invention in one or more aspects fills the aforementioned needs in the art by providing low emission and energy conserving systems and processes for producing useful fuels from a wide variety of carbon-containing source materials.

SUMMARY OF THE INVENTION

Embodiments of the present invention provide for a process, system and apparatus capable of using synthesis gas ($CO+H_2$) to produce methane, diesel fuel, and/or other hydrocarbons and useful energy. A process according to the invention comprises the gasification and/or pyrolysis of a source material to produce synthesis gas using the produced synthesis gas for the production of a hydrocarbon, methanol, ammonia, urea, and other products using Fischer-Tropsch synthesis, methanation, and other reactions. Accordingly, embodiments of the present invention preferably seek to mitigate, alleviate or eliminate one or more deficiencies, disadvantages or issues in the art, singly or in any combination by providing carbon neutral methods and systems that produce hydrocarbon fuels from carbon-containing materials, especially carbon-containing waste materials such as bioorganic (biomass) waste and organic waste (e.g. plastics). The present invention provides advantages over existing systems and processes with respect to toxic and greenhouse emissions, cost, and production.

According to one aspect of the invention, a process and system for producing a hydrocarbon fuel is provided in which the process comprises gasifying and/or pyrolizing a carbon source by plasma to form syngas; reacting a portion of the formed syngas with water in a water shift reactor to convert a portion of the syngas to $CO_2$ and $H_2$ and thereby adjust the ratio of CO to $H_2$ in the syngas; and synthesizing the hydrocarbon fuel from the produced syngas.

According to another aspect of the invention, a process and system for producing a hydrocarbon fuel is provided in which the process comprises gasifying and/or pyrolizing a carbon source by plasma to form $CO_2$ and $H_2O$; reacting a portion of the formed $CO_2$ with $H_2$ to produce CO and $H_2$ and thereby adjust the ratio of CO to $H_2$ in the syngas; and synthesizing the hydrocarbon fuel from the produced CO and $H_2$.

According to another aspect of the invention, a process and a system for producing methanol is provided in which the process comprises gasifying and/or pyrolizing a carbon source by plasma to form syngas; reacting a portion of the formed syngas with water to form $CO_2$ and $H_2$ to produce CO and $H_2$; and synthesizing methanol from the produced CO and $H_2$.

According to yet another aspect of the invention, a process and system for producing a hydrocarbon fuel is provided in which the process comprises gasifying and/or pyrolizing a carbon source by plasma to form CO and $H_2$, and synthesizing the hydrocarbon fuel from the produced CO and $H_2$.

According to yet another aspect of the invention, a process and system for producing a ammonia is provided in which the process comprises gasifying and/or pyrolizing a carbon source by plasma to form CO and $H_2$; reacting all or a portion of the formed CO with water to produce $H_2$; and synthesizing ammonia from the produced $H_2$ and nitrogen.

Additional aspects of the invention include methods, apparatus, and systems comprising combinations of the aspects of the invention to produce methane, methanol, diesel, and other chemicals; to perform Fischer-Tropsch processes, provide gas turbine fuel, and for carbon capture and storage (CCS).

Gasification/pyrolysis may be performed by any suitable means, preferably a plasma gasification means, including cool plasma and plasma gasification. Thermal catalytic gasification methods such as counter-current fixed bed ("up draft") gasification, co-current fixed bed ("down draft") gasification, fluidized bed gasification and entrained flow gasification are not suitable gasification means because synthesis gas produced using these gasification means may contain large amounts of tar that fowl catalytic systems.

Heat from reactions of synthesis gas may supply all or parts of the heat required to gasify or pyrolize carbon-containing source materials such as biological and organic waste to form synthesis gas. Through this process it is possible to gasify organic and biological waste and produce energy in a $CO_2$ neutral manner. By combining the above processes, a "reaction loop" is formed, wherein the recapture of heat produced by chemical reactions provides usable energy as electrical energy or chemical energy in the form of a fluid that may be combusted directly or stored as potential chemical energy.

An advantage of the present system and process is the reduction of $CO_2$ emissions with respect to existing gas to fuel systems and the possibility of achieving carbon neutral carbon source to fuel conversion. Another advantage of the present invention is the ability to reduce mixed oxides of nitrogen and sulfur (NOx and SOx) to nitrogen, water, and sulfur and thereby reduce or eliminate emissions of these pollutants. Yet another advantage of the present invention is the selective synthesis of hydrocarbon species in a gas to fuel reaction, such as the selective synthesis of $C_8$-$C_{14}$ hydrocarbons, by controlling catalyst composition and reactions conditions. Yet another advantage of the present invention is the ability to use raw synthesis gas produced by plasma gasification directly for water shift and/or gas to fuel reactions to produce liquid fuel. These and further advantages of the invention are described in greater detail hereinbelow.

The term "comprises/comprising" when used in this specification is taken to specify the presence of stated features, integers, steps or components but does not preclude the presence or addition of one or more other features, integers, steps, components or groups thereof.

As used herein, the term "neutral" with respect to emitted $CO_2$ means that total carbon emission to the atmosphere neither increases nor reduces during a process. One example of a carbon neutral process is plants assimilating carbon (in the form of $CO_2$) from the atmosphere and storing it in the form of cellulose, sugars, or other biomass and the combustion of the biomass in air to produce the same amount of $CO_2$ as was assimilated by the plants.

As used herein, "organic waste" refers to all waste containing organic chemicals containing carbon and hydrogen. Examples of organic waste include municipal solid waste, plastics, sewage, animal manure, and hospital waste.

As used herein "biological waste" refers to any waste of biological origin containing carbon and hydrogen. Examples of biological waste include olive pits, rice husks, bagasse, wood chips, sawdust, corn husks, and products and byproducts of agricultural and/or forestry processes including methane gas.

In the context of the present invention, "hydrocarbon fuels" refers to materials comprising any number of carbon atoms and hydrogen atoms that may react through combustion to producing energy. Specific non-limiting examples of hydrocarbon fuels include methane, methanol, ethanol, propane, butane, diesel, gasoline, and kerosene. Hydrocarbon fuels include alkanes, alcohols, alkenes, alkynes, and aromatic hydrocarbons.

In the context of the present invention, "carbon-containing source material" refers to materials comprising any number carbon atoms and hydrogen atoms in their structure that may be converted to or processed to a fluid or gaseous form or which may remain in a solid form, and which in their solid, fluid or gaseous forms may be combusted to form carbon monoxide and/or carbon dioxide and/or methane. Non-limiting examples of carbon-containing source materials include organic and biological waste as described supra, and any waste containing carbon that may be used as material for a pyrolysis or gasification process including but not limited to solid or liquid municipal waste, solid or liquid biomass, solid or liquid medical waste, solid or liquid biohazard waste, solid or liquid chemical waste, and coal.

In the context of the present invention, "combustion" refers to any reaction involving oxygen and a carbonaceous material within the temperature intervals indicated infra. In the context of the present invention the term "gasification" means the evaporation and/or combustion of organic fuel by cool plasma gasification or plasma gasification.

As used herein, "chemical energy" refers to the latent or potential energy of a compound that may be released through a chemical process that lowers the potential energy of the relevant compound forming one or more reaction products with a lower net potential energy and releasing the energy difference between the original compound(s) and the product(s).

In the context of the present invention, "electrical energy" refers to energy that may be utilized by an electrical storage unit (battery, condenser, etc.) or be converted to other forms of energy, e.g. mechanical energy, through the use of an electrical appliance. In the context of the present invention, the term "large amounts of energy" refers to energy within the range 5-50 MJ/kg. The term "large amounts" of chemical energy in the context of the present invention, is an energy difference between original and product compounds that represents at least 15% of the chemical energy of the original compound(s).

In the context of the present invention the term "about" refers to a relative deviation from the indicated amount of up to ±10%, i.e. an interval of one unit per ten units of the relevant number. The deviation may also be smaller, e.g. 1%, 2%, 3%, 4%, 5%, 6%, 7%, 8% or 9% or any number in between or any interval combination thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DETAILED DESCRIPTION OF THE INVENTION

Figure 1:
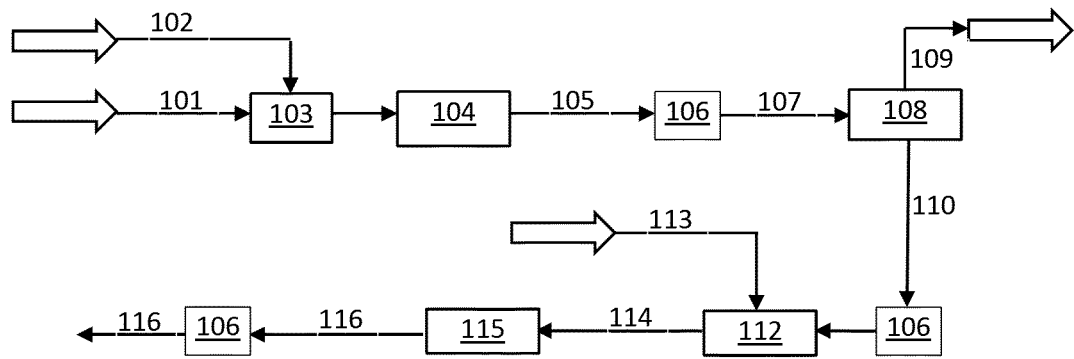
FIG. 1 is schematic of a system and process for gasification of biomass using air as a gasification gas and FIG. 2 is schematic of a Gas to Fuel Process system and process for the production of diesel.

Specific embodiments of the invention are described with reference to the accompanying drawings. This invention may, however, be embodied in many different forms and should not be construed as limited to the embodiments set forth herein. Rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The following description focuses on an embodiment of the present invention applicable to a process and system for the synthesis of a hydrocarbon fuel and in particular to a process and system for the synthesis of diesel fuel, methane, and/or methanol. However, it will be appreciated that the invention is not limited to this application but may be applied to the synthesis of many other products including, for example jet fuel, gasoline, propane, butane, ammonia, urea, ethanol, and propanol.

A first stage in one embodiment according to the invention comprises the production of synthesis gas from a carbon-containing material by gasification and/or pyrolysis. A process and system for the first stage of such an embodiment is shown in FIG. 1. This embodiment of the invention provides for energy recapture to provide usable energy as well as providing a gas that may be combusted or that contains large amounts of chemical energy.

A feed of carbon-containing source material 101 is mixed with a feed of air, steam, and/or an oxygen-containing gas 102 in a mixer 103 and introduced into a gasifier 104. The gasifier 104 is configured to produce a feed comprising CO and $H_2$ (syngas) 105. Examples of gasifiers that are suitable for commercial production of clean syngas according to the invention include cool plasma gasifiers and plasma gasifiers. The first stage of the process shown in FIG. 1 may comprise catalysts and other devices that produce syngas. Syngas contains $H_2$ and CO and, depending on the source materials and reactions, may also contain on or more of $CO_2$, $H_2O$, $N_2$, NOx, SOx, and $CH_4$.

Cool plasma gasification or pulsed plasma gasification effectively breaks down organic molecules into synthesis gas. Unlike gasifiers that rely solely on heat to provide molecular disassociation, temperature plays only a partial role in cool-plasma gasification. A plasma field is created in an oxygen-starved environment that generates a temperature of approximately 1,300° C. at the bottom end of the plasma arc spectrum. Biomass or organic waste is passed directly through the plasma field in such a way that both temperature and plasma dynamics combine to accomplish molecular disassociation. The plasma field is pulsed to create shock waves and molecular temperatures as high as 15,000° C. to 50,000° C., while the average temperature is maintained at 1300° C. The shock waves and high temperatures break down longer and complex molecular chains, resulting in the reduction of the raw feedstock into its elemental components. The relatively low average temperature allows an energy recovery of around 90%.

Plasma gasification is used to break down waste materials that are infectious or in other ways pose an environmental hazard. High voltage, high current electricity is passed between two electrodes that are spaced apart, creating an electrical arc. Consequently, the process is more expensive and is associated with lower energy recovery (around 50%) than cool plasma gasification. Inert gas or gas with low oxygen content under pressure is passed through the arc into a sealed container of waste material. The temperature may be as high as 14,000° C. in the arc column, while the temperature a few feet from the torch can be as high as 2800° C.-5000° C. At these temperatures, most wastes are dissociated into elemental components in a gaseous form. The reactor operates at a slightly negative pressure, meaning that the feed system is complemented by a gas removal system, and also a solid removal system. In the case of plastic wastes, which tend to be high in hydrogen and carbon, gas from the plasma containment can be removed as syngas, and may be refined into various fuels at a later stage or used on site to provide power. Syngas is produced from organic materials with a conversion rate of greater than 99% using plasma gasification. Inorganic materials in the waste stream that are not broken down undergo a phase change (e.g. from solid to liquid) to form a slag. A portion of the syngas may be used to run an on-site turbine to power plasma torches and feed systems.

Gasification of organic material according to the present invention is preferably performed with low levels of $O_2$, i.e. $O_2$ concentrations of the inlet gas in the range of 0.5%-15% $O_2$ (v/v), but may also be performed by using exhaust gas, from a combustion process for example, with low levels of water and oxygen, by using water or steam, or by using pure oxygen at a level that will produce syngas. Any combination of the gases supra may be used. Gasification of the carbon-containing source material may be performed at a temperature in the range of 500° C.-5000° C., preferably within the range of 1000-5000° C., e.g. within the range of 500° C.-1000° C., 1000°-1500° C., 1500° C.-2500° C., 2500° C.-3500° C., or 3500° C.-5000° C. The gasification pressure may range from 0.5 bar to 10 bar. The inclusion of, for example, exhaust gas containing $CO_2$ and $H_2O$ in the feed increases the production of synthesis gas by the reaction $C+CO_2 \rightarrow 2CO$ and $C+H_2O \rightarrow CO+H_2$.

The temperature of the syngas feed leaving the gasifier may be in the range of 100° C.-2000° C., depending on the conditions and starting materials selected. Examples of selected temperature ranges for the combustion products include 200° C.-1800° C., 300° C.-1500° C., 400° C.-1300° C., 500° C.-1250° C., 550° C.-1200° C., 600° C.-1100° C., 700° C.-1000° C. or any combination of these. If the temperature of the synthesis gas leaving the gasifier is high enough, a heat exchanger 106 may be used to generate electrical energy or supply heat for producing steam and to produce a cooled syngas feed 107. Water that may be present in cooled syngas feed 107 may be removed in separator 108 to separate condensed water 109 from syngas feed 110.

Syngas feed 110, optionally preheated by optional heat exchanger 106, is mixed with steam 113 in mixer 112 to form a mixture of steam, $H_2$, and CO 114, which enters a water gas shift reactor 115 where the steam and CO react to form $CO_2$ and $H_2$. This effectively alters the ratio of $H_2$ to CO such that the ratio is raised, for example, to 2:1. The operation of the water gas shift reactor 115 may be controlled to produce a syngas feed having a desired $H_2$:CO ratio which may range, for example, from 1:4 to 4:1. The final ratio may be selected based upon the fuel to be synthesized in the second stage of the process. The shift reaction may occur in a low temperature reactor or a high temperature reactor wherein CO reacts with steam over a suitable catalyst to produce $CO_2$ and $H_2$. Examples of suitable catalysts are iron oxide/chromium oxide and copper oxide/zinc oxide catalysts for low and high temperature reactors, respectively. The produced syngas, which now comprises $H_2$ and CO in a desired ratio, e.g. 2:1, and $CO_2$, provides a syngas feed 116 for a second stage of the process shown in FIG. 2. A heat exchanger 106 may be placed downstream of water gas shift reactor 115 to be used as the heat exchanger upstream of separator 108 and may also be used to maintain products of the reactor 115 at a desired temperature.

It is also possible to configure a gasification system that produces a synthesis gas comprising $H_2$, CO, and $CO_2$ having a desired $H_2$:CO ratio by proper selection of, for example, the carbon-containing material for gasification, the concentration of oxygen present during gasification, the amount of water present in the carbon-containing material and/or during gasification, to effectively combine the water gas shift reaction into the gasification process. In such embodiments, the water gas shift reactor may be dispensed with and the synthesis gas produced by gasification may be used to provide a synthesis gas feed stream 116 for a second stage of the process shown in FIG. 2.

Figure 2:
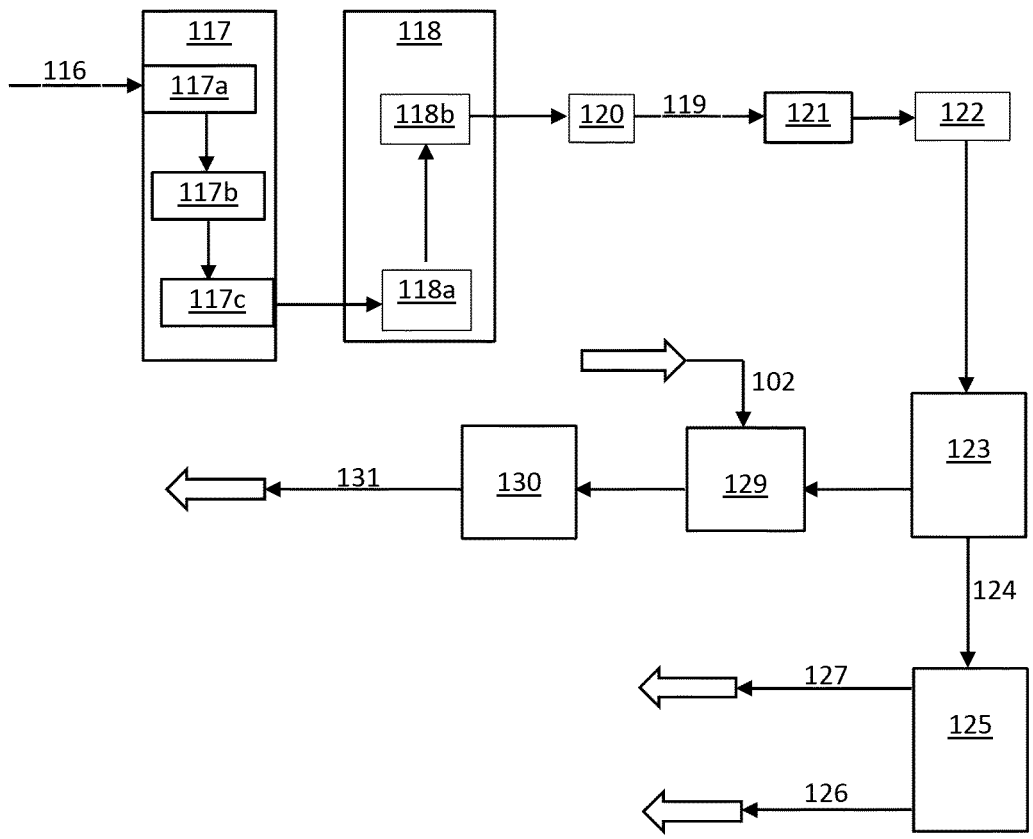

A system for performing a second stage of a process according to the invention is shown in FIG. 2. A syngas feed 116 is compressed by a compressor 117 before being conveyed into a gas to fuel reactor 118 where the syngas is converted to a fuel-containing feed stream 119. The embodiment shown comprises a two stage compressor 117 comprising two compressors 117a, 117b with an optional heat exchanger 117c located between the two compressors to remove heat and cool the syngas to a temperature of. The compressor however, need not be a two-stage compressor, which is used for the purpose of describing this specific embodiment of the invention. The gas to fuel reactor 118 is shown comprising two rector vessels 118a and 118b but other embodiments may comprise more of fewer reactors (reactor vessels) arranged in series and/or in parallel and performing the same of different chemical reactions. In the case of exothermic reactions taking place in the gas to fuel reactor, an optional heat exchanger 120, which may be integrated in the reactor 118, may be used to cool the fuel-containing feed stream 119 and provide heat for electrical energy production and plasma gasifier operation and/or heat for steam production.

The embodiment shown in FIG. 2 may be configured, for example, for the production of gasoline, kerosene, and/or diesel by exothermic reactions. While embodiments for the production of diesel and other specified fuels are described herein, the invention is not intended to be limited to the specific embodiments described. In the embodiment shown, the cooled fuel-containing feed 119 may contain, in addition to diesel, methane, ethane, $CO_2$, and unreacted syngas. The cooled fuel-containing feed stream 119 is conveyed to and expanded in turbine 121, optionally cooled in heat exchanger 122, and separated into liquid and gaseous components 124, 128 in separator 123. The gaseous components 128, including methane, ethane, $CO_2$, and syngas are mixed with an air feed 102 in mixer 129 and conveyed to a power generator 130 where they are combusted to provide, for example, electrical energy and combustion products 131. The liquid components 124 may be conveyed to a distillation apparatus 125 where diesel, water, and other liquid components are separated to produce diesel and water outlet streams 126, 127.

The diesel synthesis reaction performed in the gas to fuel reactor 118 preferably uses a gas composition comprising a $H_2$/CO ratio of about 2. The primary reaction for the formation of diesel from synthesis gas is:

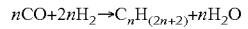
$$nCO+2nH_2 \rightarrow C_nH_{(2n+2)}+nH_2O$$

where n has a value of 14-20. During CO hydrogenation, other products may be formed, such as higher alcohols and hydrocarbons. The selectivity of known catalysts for the reaction is over 80%. Diesel synthesis is performed at pressures above 25 bar at temperatures normally not exceeding 570K. The ratio of $H_2$ may be controlled by the water gas shift reactor 115. Additionally or alternatively, the ratio of $H_2$/CO may be adjusted by providing an additional hydrogen-rich feed from a source of hydrogen production.

In some embodiments, the catalyst in the gas to fuel reactor 118 comprises Fe metal alloyed with Co metal and/or Ru metal coated on a support and comprising an amount of a promoter selected from the group of Pd, Pt, Cu, Rh, Ir, Ag, W, Ir, and combinations thereof. The weight percent of Fe, Co, and or Ru present in the catalyst is 20-80%. The weight percent of promoter in the catalyst may range from 0.01%-10% or preferably 0.01% to 1.0%. The use of such catalysts unexpectedly narrows the distribution of produced alkanes/paraffins in a temperature, pressure and residence time dependent manner. This allows a greater control of products formed from synthesis gas in the gas to fuel reactor with respect to existing processes, systems, and catalysts.

The same catalyst may be, but need not be, used in both the water gas shift reactor 115 and the gas to fuel reactor 118. It is also possible to perform the water gas shift reaction and the gas to fuel reaction simultaneously in a single reactor.

In addition to diesel, synthesis gas may be converted to a wide range of hydrocarbons and/or alcohols in gas to fuel reactor 118 through one or more F-T process reactions:

Alkanes: $nCO+(2n+1)H_2 \rightarrow C_nH_{2n+2}+nH_2O$

Alkenes: $nCO+2nH_2 \rightarrow C_2H_{2n}+nH_2O$

Water-gas shift: $CO+H_2O \rightarrow CO_2+H_2$

Alcohols*: $nCO+2nH_2 \rightarrow H(-CH_2-)_nOH+(n-1)H_2O$

Bouoduard reaction*: $2CO \rightarrow C+CO_2$

* side reactions

One characteristic of F-T reactions is that they are highly exothermic. For example, the formation of 1 mol of —$CH_2$— is accompanied by a release of 165 kJ/mol of heat. Efficient removal of the heat of reaction is a consideration in the selection/design of suitable Fischer-Tropsch reactors. For example, fixed-bed and slurry reactors operate at relatively low temperatures, up to about 530 K and up to about 570 K, respectively, resulting in a selectivity towards heavy products (waxes), which may be cracked to produce lighter products. A low $H_2/CO$ ratio in the slurry reactor results in a relatively high selectivity towards liquid products. The riser reactor operates at higher temperatures, usually above 570 K, and produces gasoline as a major product as well as light products such as methane. Any of these reactors may be included alone or in combination in the gas to fuel reactor 118.

The reaction performed in reactor 118 may also be a methanation reaction performed in the presence of Ni/NiO, Ru, Cu, Pt, Rh, Ag, Co, and/or W catalyst in the temperature range of 150° C. to 600° C. and pressures of from 1 bar to 50 bar. CO and $CO_2$ react with $H_2$ to form methane and water according to Methanation Reactions 2 and 3 in Table 1. The catalyst may also suppress the reverse shift reaction 4. The methane produced may be used as a fuel or as a raw material for the production of methane, diesel, ammonia, urea, nitric acid, ammonium nitrate, NPK, and PVC, for example. Reactors for these syntheses may be coupled to a fuel outlet 126 (FIG. 2) in an embodiment producing methane. The $H_2$ and CO produced may also be used as raw materials for other uses and processes.

The processes according to the present invention may be performed within a reactor for providing ways of controlling the physical and chemical parameters involved in the reaction equations shown in Table 1.

TABLE 1

| | |
|---|---|
| $CO + H_2O \rightarrow CO_2 + H_2$ | Shift reaction 1 |
| $CO + 3H_2 \rightarrow CH_4 + H_2O$ | Methanation reaction 2 |
| $CO_2 + 4H_2 \rightarrow CH_4 + 2H_2O$ | Methanation reaction 3 |
| $CO_2 + H_2 \rightarrow CO + H_2O$ | Reverse shift reaction 4 |
| $C + H_2O \rightarrow H_2 + CO$ | Gasification reaction 5* |
| $C_xH_y + (x + y/4)O_2 \rightarrow xCO_2 + (y/2)H_2O$ | Combustion reaction 6 |
| $nCO + 2nH_2 \rightarrow C_nH_{(2n+2)} + nH_2O$ | Diesel reaction 7 |

*C is any organic substance like, but not limited, to biomass or organic waste.

Ratios of reactants in the gas to fuel rector(s) 118 may be controlled by providing addition streams of reagents and/or by way of one or more reactor vessels included in the gas to fuel reactor 118. For example, a reactor producing $H_2$ and CO according to reaction 5 may provide $H_2$ to a reaction vessel that is provided with additional $H_2$, directly or indirectly, from a reaction vessel producing $H_2$ in which reaction 1 takes place. Produced $H_2$ may also be reacted with CO and $CO_2$ in a single or in separate reaction vessels according to reaction 2 and 3 to produce methane. The reactions and reaction vessels in the gas to fuel reactor may be configured according to the product(s) to be synthesized using reactions 1-7 in Table 1 without relying on energy consuming processes for producing $H_2$ such as water splitting.

The system and process may comprise more than one gasifier 104, for example arranged in parallel, using different carbon source materials and or different oxygen concentrations to produce streams of syngas comprising different $CO:H_2$ ratios. The different streams of syngas may be blended in a controlled manner before being fed into, for example, gas to fuel reactor(s) 118.

Reacting CO and/or $CO_2$ with $H_2$ to produce methane may be performed in a single reactor with a catalyst. The heat developed may be used for gasification, steam production, and/or generating electricity. The shape of the catalyst is not critical and may inter alia comprise coated monoliths, nano materials, and/or other types and forms of carriers. The carriers may be selected from e.g. $TiO_2$, $Al_2O_3$, cordierite, and Gd-doped CeO. The catalytic material may also be present in any form as a "pure" catalyst material. The form and composition of the reactor and the catalyst depends on the source of CO and/or $CO_2$. If the source is an impure exhaust gas with large amounts of dust (e.g. from the combustion of coal) a monolithic catalyst carrier may be used, whereas a catalyst in the form of pellets may be used with a pure exhaust gas (e.g. from a natural gas turbine). All types of exhaust gases from all types of combustions of organic material may be used as a source material for the second stage gas to fuel reactor 118 (FIG. 2) to produce methane. Examples of usable catalysts include Ni/NiO, Ru, Cu, Pt, Rh, Ag, Co, and W and/or oxides of the described elements catalysts and combinations thereof.

In some embodiments of the invention it is possible to produce nitrogen containing compounds such as ammonia and urea using known chemical syntheses. For example, $H_2$ may be separated from CO and/or $CO_2$ produced by gasifier 104 and reacted with oxygen depleted air or nitrogen in an exhaust gas:

$N_2+3H_2 \rightarrow 2NH_3$

The present invention is also useful for the sequestration of $CO_2$ produced by the burning of fossil fuels. During gasification in gasifier 104 (FIG. 1) $CO_2$ may react with carbon in the carbon-containing source material to form CO, which is ultimately used in the gas to fuel reactor 118 to produce diesel fuel, for example. $CO_2$ produced by fossil fuel combustion may alternatively or additionally enter the process/system in stream 102 (FIG. 1) with or without addition of air and/or oxygen and/or steam. For example, in one embodiment of the invention, a fossil fuel is combusted with air in a burner or combustor and electricity is produced from the combustion process in a conventional manner. The exhaust, containing $H_2O$ and $CO_2$, is cooled to condense and remove $H_2O$. An ordinary concentration of $CO_2$ in the combustion gas is about 1-20% by volume. $CO_2$ from the exhaust is used as a feed in addition to feed 116 into reactor 118 for methane production according to reaction 3 or reactions 2 and 3 in Table 1. The methane produced is recirculated while the hydrogen and CO produced by the gasification is used for producing methanol.

The combustion/gasification of organic waste, biomass, biological waste, and fossil fuels often produces nitrogen-containing gases such as NOx, which may treated by selective non-catalytic reduction, selective catalytic reduction, and other NOx-reducing apparatus known to the skilled artisan. NOx and SOx may also be present in a gasification or pyrolysis exhaust gas. An advantage of the present process is that these pollutants can be reduced to elemental nitrogen and sulfur in the gas to fuel reactor(s) 118 and thereby reduce air pollution compared to existing processes. Reduction of NOx and SOx may be achieved by one or more of the following reactions with synthesis gas:

$$NO_2 + 2H_2 \rightarrow \tfrac{1}{2}N_2 + 2H_2O$$

$$NO_2 + 2CO \rightarrow \tfrac{1}{2}N_2 + 2CO_2$$

$$NO + H_2 \rightarrow \tfrac{1}{2}N_2 + H_2O$$

$$NO + CO \rightarrow \tfrac{1}{2}N_2 + CO_2$$

Sulfur present in an exhaust stream from the combustion of high sulfur coal, sulfur containing biomass, or sulfur containing municipal waste may be reduced by reaction with carbon in a gasifier 104 or additional gasifier according to the reaction $$SO_2 + 2C \rightarrow S + 2CO$$

with the resulting CO optionally being fed into stream 116 for use in the gas to fuel reactor 118.

The invention claimed is:

1. A process for producing a fuel comprising:
    gasifying a carbon-containing material in a cool plasma gasifier to produce a first synthesis gas comprising $H_2$ and CO and having a first mol:mol ratio of $H_2$ to CO;
    reacting said first synthesis gas with steam in a water gas shift reactor to produce a second synthesis gas comprising $CO_2$, $H_2$ and CO, said second synthesis gas having a second mol:mol ratio of $H_2$ to CO that is greater than said first ratio of $H_2$ to CO in said first synthesis gas; and
    reacting $H_2$ and CO in the second synthesis gas in a gas to fuel reactor to produce a hydrocarbon and/or an alcohol.

2. The process according to claim 1, wherein said hydrocarbon and/or alcohol is methane, ethane, propane, butane, diesel fuel, a jet fuel, a kerosene fuel, a gasoline, methanol, ethanol, or propanol.

3. The process according to claim 1, wherein the second mol:mol ratio of $H_2$ to CO is about 2:1 and said reacting $H_2$ and CO in the second synthesis gas in the gas to fuel reactor produces one or more hydrocarbons containing from 8 to 20 carbon atoms.

4. The process according to claim 1, wherein said gasifying a carbon-containing material in said cool plasma gasifier produces a first synthesis gas having a temperature of from 1000° C. to 1500° C.

5. The process according to claim 1, wherein the gas to fuel reactor comprises a catalyst comprising an alloy of Fe and Co or an alloy of Fe and Ru and a promoter selected from the group consisting of Pd, Pt, Cu, Rh, Ir, Ag, W, Ir, and combinations thereof.

6. The process according to claim 5, wherein Fe is present in the catalyst in an amount of from 20 to 80 weight percent and at least one of Co and Ru is present in the catalyst in an amount of from 20 to 80 weight percent.

7. The process according to claim 6, wherein said promoter is present in the catalyst in an amount of from 0.01 to 10 weight percent.

8. The process according to claim 1, and further comprising feeding a combustion exhaust into the cool plasma gasifier and/or the gas to fuel reactor.

9. The process according to claim 1, and further comprising feeding a combustion exhaust into the water gas shift reactor.

10. The process according to claim 1, further comprising reducing mixed oxides of nitrogen in the gas to fuel reactor to form nitrogen or further comprising reducing mixed oxides of sulfur in the gas to fuel reactor to form sulfur.

11. The process according to claim 1, and further comprising feeding sulfur dioxide into the cool plasma gasifier and reacting said sulfur dioxide with carbon in the gasifier to produce sulfur and CO.

12. The process according to claim 1, wherein the carbon-containing material is selected from a solid municipal waste, a liquid municipal waste, a solid biomass, a liquid biomass, a solid medical waste, a liquid medical waste, a solid biohazard waste, a liquid biohazard waste, a solid chemical waste, a liquid chemical waste, coal, and combinations thereof.

13. The process according to claim 1, wherein the gas to fuel reactor produces methane, the second mol:mol ratio of $H_2$ to CO is about 2:1, and the reaction comprises:

$$CO + 3H_2 \rightarrow CH_4 + H_2O$$

and/or $$CO_2 + 4H_2 \rightarrow CH_4 + 2H_2O.$$

* * * * *